United States Patent
Graham et al.

(10) Patent No.: US 8,357,129 B2
(45) Date of Patent: Jan. 22, 2013

(54) SKIN REJUVENATION SYSTEM AND METHOD

(75) Inventors: Janet R. Graham, Morgan Hill, CA (US); Douglas A. Ginter, Morgan Hill, CA (US)

(73) Assignee: Physicans Products, Inc., San Jose, CA (US)

( * ) Notice: Subject to any disclaimer, the term of this patent is extended or adjusted under 35 U.S.C. 154(b) by 156 days.

(21) Appl. No.: 12/943,552

(22) Filed: Nov. 10, 2010

(65) Prior Publication Data
US 2011/0112491 A1    May 12, 2011

Related U.S. Application Data

(60) Provisional application No. 61/260,573, filed on Nov. 12, 2009.

(51) Int. Cl.
*A61H 33/04* (2006.01)

(52) U.S. Cl. ........ 604/303; 604/304; 604/307; 604/358; 604/368; 424/401; 424/449; 514/163; 514/241

(58) Field of Classification Search ............... 604/303, 604/304, 307, 358, 368; 424/401, 449; 514/163, 514/241
See application file for complete search history.

(56) References Cited

U.S. PATENT DOCUMENTS

| | | | | |
|---|---|---|---|---|
| 4,294,241 | A * | 10/1981 | Miyata | 602/50 |
| 4,585,797 | A * | 4/1986 | Cioca | 514/773 |
| 2003/0064093 | A1* | 4/2003 | Jordan | 424/449 |
| 2003/0134780 | A1* | 7/2003 | Patt | 514/6 |
| 2005/0013784 | A1* | 1/2005 | Trigg et al. | 424/62 |
| 2007/0172431 | A1* | 7/2007 | Galumbeck | 424/47 |
| 2008/0305055 | A1* | 12/2008 | Baschong et al. | 424/59 |
| 2011/0305736 | A1* | 12/2011 | Wieland et al. | 424/401 |

* cited by examiner

*Primary Examiner* — Jacqueline F Stephens
*Assistant Examiner* — Andrew J Mensh
(74) *Attorney, Agent, or Firm* — Edward S. Wright

(57) ABSTRACT

Skin rejuvenation system and method in which a pure plant collagen carrier is saturated with a solution of collagen, allantoin, amino acid, propanediol, glycerin, algae, plant DNA living cells, epidermal growth factor, Vitamin E, hyaluronic acid, rose essential, water, and peptide, and the saturated carrier is applied to the skin to be rejuvenated.

10 Claims, 1 Drawing Sheet

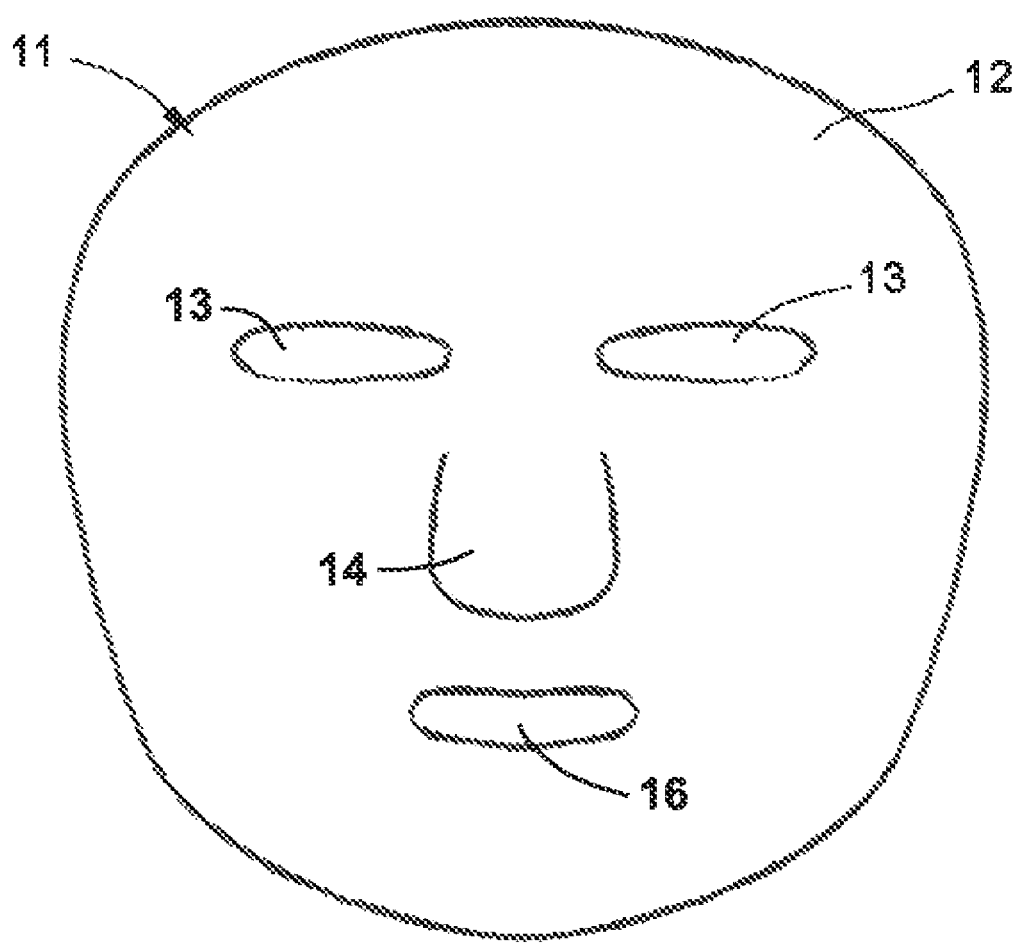

SKIN REJUVENATION SYSTEM AND METHOD

RELATED APPLICATION

Provisional Application No. 61/260,573, filed Nov. 12, 2009, the priority of which is claimed.

BACKGROUND OF THE INVENTION

1. Field of Invention

This invention pertains generally to skin rejuvenation and, more particularly, to a system and method for rejuvenating facial skin and skin on other parts of the body as well.

2. Related Art

Heretofore, a wide variety of compositions and treatments have been employed for rejuvenating the skin to give it a more youthful appearance. Older skin does not regenerate itself as quickly as younger skin, and aging brings undesirable changes in the tone and texture of the skin. In addition, collagen and elastin fibers in the underlying layers of the skin tend to weaken and deteriorate with age, causing the skin to lose elasticity and sag as well as developing unsightly lines and wrinkles.

OBJECTS AND SUMMARY OF THE INVENTION

It is, in general, an object of the invention to provide a new and improved skin rejuvenation system and method.

Another object of the invention is to provide a skin rejuvenation system and method of the above character which improve collagen production and total skin hydration.

These and other objects are achieved in accordance with the invention by providing a skin rejuvenation system and method in which a pure plant collagen carrier is saturated with a serum consisting essentially of plant derived collagen and other all natural ingredients, and the saturated carrier is applied to the skin to be rejuvenated.

BRIEF DESCRIPTION OF THE DRAWING

The single figure of drawings is a front elevational view of one embodiment of a facial mask or carrier according to the invention.

DETAILED DESCRIPTION

The facial mask or carrier 11 has a body 12 with eye openings 13, a nose flap 14, and a mouth opening 16. It is made of pure plant collagen and is flexible and compliant when applied to the face of a user.

The mask is saturated with a solution or serum which in one presently preferred embodiment has the following composition:

| Material | Percent by Volume |
| --- | --- |
| Collagen | 2.50 |
| Allantoin | 0.50 |
| Amino Acid | 2.00 |
| Propanediol | 4.00 |
| Glycerin | 3.00 |
| Algae | 2.00 |
| Plant DNA Living Cells | 1.00 |
| Epidermal Growth Factor | 0.20 |

-continued

| Material | Percent by Volume |
| --- | --- |
| Vitamin E | 0.50 |
| Hyaluronic Acid | 0.20 |
| Rose Essential | 0.01 |
| Water | 84.00 |
| Peptide | 0.09 |

This unique combination of all natural ingredients with a pure plant collagen delivery system transforms the skin by nourishing the epidermal layer and penetrating the top layers of skin to increase collagen production and total skin hydration. It produces an immediate smoothing and firming of the skin, and with continued use, the skin will be more hydrated, pore size will be dramatically reduced, and wrinkles will seem to vanish from the inside out. The skin will feel supple and look radiant and clear.

Plant derived collagen is an important ingredient for healthy skin, and the combination of the plant collagen mask delivery system and the plant collagen serum may even promote new collagen production. As a result, the skin will be luminous, clear, toned and hydrated.

The hyaluronic acid in the serum is a super hydrator for the skin. It targets deep wrinkles, increases firmness and elasticity while also boosting collagen and elastin production.

The peptides aid in softening and smoothing wrinkles, promoting moisture retention and help skin recover from sun and environmental damage.

The epidermal growth factor promotes firmness, refines skin texture, and reduces fine lines as it increases cell regeneration.

The living plant DNA repairs damage to the skins' DNA from environmental stresses. It helps minimize pore size and smooths overall complexion and blemish scars while combating sun damage.

The algae has remarkable skin lifting properties, soothing and nourishing all skin types with natural seaweed and phytoplankton.

Vitamin E is a powerful antioxidant which combats free radicals and helps prevent further skin damage, providing a virtual shield for the skin.

It is contemplated that the mask will be pre-saturated with the serum or solution and distributed in a sealed bag, ready for use. The mask is removed from the bag and applied to the skin with the wearer in a face-up, reclined position. Because of the compliancy of the mask, it follows the contours of the face closely, with no notches around the edges and nothing else to hold it in place.

Although the invention has been described with specific reference to a facial mask, it can also be applied to other parts of the body such as the neck and the décolleté area, and in more localized areas such as under the eyes. In such applications, the mask and the solution or serum have the same compositions as the facial mask and serum, and the masks are configured in accordance with the areas they are to cover.

The invention has a number of important features and advantages. The unique combination of all natural ingredients with a pure plant collagen delivery system transforms the skin by nourishing the epidermal layer and penetrating the top layers of skin to increase collagen production and total skin hydration. It produces an immediate smoothing and firming of the skin on the face, the neck, the décolleté area, under the eyes, or wherever it is used, and with continued use, the skin will be more hydrated, pore size will be dramatically reduced, and wrinkles will disappear.

It is apparent from the foregoing that a new and improved skin rejuvenation system and method have been provided. While only certain presently preferred embodiments have been described in detail, as will be apparent to those familiar with the art, certain changes and modifications can be made without departing from the scope of the invention as defined by the following claims.

The invention claimed is:

1. A skin rejuvenation system comprising a flexible mask made of pure plant collagen saturated with a serum containing collagen, allantoin, amino acid, propanediol, glycerin, algae, plant DNA living cells, epidermal growth factor, Vitamin E, hyaluronic acid, rose essential, water, and peptide.

2. The skin rejuvenation system of claim 1 wherein the serum consists essentially of 2.50% collagen, 0.50% allantoin, 2.0% amino acid, 4.0% propanediol, 3.0% glycerin, 2.0% algae, 1.0% plant DNA living cells, 0.20% epidermal growth factor, 0.50% Vitamin E, 0.20% hyaluronic acid, 0.01% rose essential, 84.0% water, and 0.09% peptide by volume.

3. The skin rejuvenation system of claim 1 wherein the mask is a facial mask.

4. The skin rejuvenation system of claim 3 wherein the facial mask has a body with eye openings, a nose flap, and a mouth opening, and is flexible and compliant when applied to a face.

5. A skin rejuvenation method comprising the steps of saturating a pure plant collagen carrier with a solution of collagen, allantoin, amino acid, propanediol, glycerin, algae, plant DNA living cells, epidermal growth factor, Vitamin E, hyaluronic acid, rose essential, water, and peptide, and applying the saturated carrier to skin to be rejuvenated.

6. The method of claim 5 wherein the saturated carrier is applied to facial skin.

7. The method of claim 5 wherein the saturated carrier is applied to skin on a part of the body other than the face.

8. A skin rejuvenation system comprising a flexible mask made of pure plant collagen saturated with a serum consisting essentially of plant derived collagen and other all natural ingredients for nourishing the epidermal layer and penetrating the top layers of skin to increase collagen production and total skin hydration.

9. The skin rejuvenation system of claim 8 wherein the mask is a facial mask.

10. The skin rejuvenation system of claim 9 wherein the facial mask has a body with eye openings, a nose flap, and a mouth opening, and is flexible and compliant when applied to a face.

* * * * *